United States Patent
Seto et al.

(10) Patent No.: US 9,540,762 B2
(45) Date of Patent: Jan. 10, 2017

(54) ODOR ELIMINATING CLOTH AND PROCESS FOR PRODUCING THE SAME

(71) Applicant: Suminoe Textile Co., Ltd., Osaka-shi (JP)

(72) Inventors: Yasutaro Seto, Osaka (JP); Shuichi Gennaka, Nara (JP); Mayumi Ozawa, Osaka (JP)

(73) Assignee: Suminoe Textile Co., Ltd., Osaka-shi (JP)

(*) Notice: Subject to any disclaimer, the term of this patent is extended or adjusted under 35 U.S.C. 154(b) by 134 days.

(21) Appl. No.: 14/465,275

(22) Filed: Aug. 21, 2014

(65) Prior Publication Data

US 2014/0363571 A1 Dec. 11, 2014

Related U.S. Application Data

(62) Division of application No. 12/086,255, filed as application No. PCT/JP2006/317498 on Sep. 5, 2006, now abandoned.

(30) Foreign Application Priority Data

Dec. 8, 2005 (JP) ................................. 2005-354249

(51) Int. Cl.
*D06M 11/32* (2006.01)
*A61L 9/01* (2006.01)
*D06M 11/36* (2006.01)
*D06M 11/79* (2006.01)
*D06M 13/50* (2006.01)

(52) U.S. Cl.
CPC ................. *D06M 11/32* (2013.01); *A61L 9/01* (2013.01); *D06M 11/36* (2013.01); *D06M 11/79* (2013.01); *D06M 13/50* (2013.01)

(58) Field of Classification Search
CPC ....... D06M 11/36; D06M 11/32; D06M 11/79; D06M 13/50
See application file for complete search history.

(56) References Cited

U.S. PATENT DOCUMENTS 2,019,420 A * 10/1935 Lejeune et al. ............... 427/324
5,817,300 A   10/1998 Cook et al.
(Continued)

FOREIGN PATENT DOCUMENTS

JP   06-341060    12/1994
JP   10-292258    11/1998
(Continued)

OTHER PUBLICATIONS

International Search Report mailed Oct. 3, 2006, issued on PCT/JP2006/317498.
(Continued)

*Primary Examiner* — Nathan Empie
(74) *Attorney, Agent, or Firm* — Locke Lord LLP

(57) ABSTRACT

An odor eliminating cloth according to this invention is characterized in that an odor eliminating composition containing a porous inorganic substance, a metallic oxide, and an inorganic silicon compound carrying a polyamine compound is fixed to at least a part of a cloth by means of a binder resin. With this odor eliminating cloth, any types of odors of basic gases, acidic gases, neutral gases, sulphur series gases contained in the air of a room can be effectively eliminated.

2 Claims, 1 Drawing Sheet

(56) References Cited

U.S. PATENT DOCUMENTS

| | | | |
|---|---|---|---|
| 6,077,794 A * | 6/2000 | Tabata et al. | 442/123 |
| 6,521,553 B1 | 2/2003 | Tabata et al. | |
| 2004/0219126 A1 | 11/2004 | Seto et al. | |
| 2005/0136082 A1* | 6/2005 | Soane et al. | 424/401 |
| 2005/0215420 A1* | 9/2005 | Collier | A61L 9/014 502/64 |
| 2008/0276804 A1 | 11/2008 | Sayari et al. | |

FOREIGN PATENT DOCUMENTS

| | | |
|---|---|---|
| JP | 11-046965 | 2/1999 |
| JP | 11-172574 | 6/1999 |
| JP | 2000-107275 | 4/2000 |
| JP | 2000-279500 A | 10/2000 |
| JP | 2001098466 A * | 4/2001 |
| JP | 2002069837 A | 3/2002 |
| JP | 2002-153545 | 5/2002 |
| JP | 2003-125919 | 5/2003 |
| JP | 2003-336170 | 11/2003 |
| JP | 2004-313584 | 11/2004 |
| JP | 2005-198684 | 7/2005 |
| WO | WO-2004/058311 | 7/2004 |

OTHER PUBLICATIONS

Office Action dated Aug. 3, 2016, issued for German patent application No. 11 2006 003 212.7 and English translation thereof.

* cited by examiner

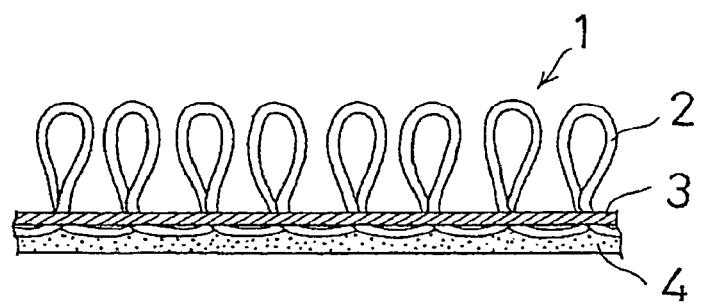

ODOR ELIMINATING CLOTH AND PROCESS FOR PRODUCING THE SAME

CROSS REFERENCE TO RELATED APPLICATIONS

This application is a Divisional application of U.S. patent application Ser. No. 12/086,255, filed Jun. 9, 2008, which application is a 35 U.S.C. §371 National Phase Application of International PCT Patent Application No. PCT/JP2006/317498, filed Sep. 5, 2006, which application claims the benefit of priority to Japanese Patent Application No. JP 2005-354249, filed Dec. 8, 2005 the contents of each of which in their entirety are hereby incorporated herein by reference.

FIELD OF THE INVENTION

The present invention relates to an odor eliminating cloth capable of effectively eliminating any types of odors of basic gases (e.g., ammonia gases, trimethylamine gases), acidic gases (e.g., acetic acid gases), neutral gases (e.g., acetaldehyde gases, formaldehyde gases), and sulphur series gases (e.g., hydrogen sulfide gases, mercaptan series gases) contained, for example, in the air of a room. It also related to a manufacturing method of the odor eliminating cloth.

BACKGROUND TECHNIQUE

A newly built recent housing is extremely improved in air-tightness, and it is said to require a time several times longer than that required for a conventional housing to replace the room air. Such high air-tightness causes easy trapping of odors in a room, resulting in discomfort. Thus, problems on living odors have become a big concern for modern people. Furthermore, a request for eliminating various odors in a room space of, e.g., an automobile, a train and an airplane has been increased.

In order to eliminate living life odors in a room, a cloth member, such as, e.g., a curtain and a carpet having an odor eliminating function has been proposed (see Patent Documents 1 to 3).

Patent Document 1 discloses an odor eliminating carpet in which a hydrazide compound, such as, e.g., adipic acid dihydrazide, is applied to and fixed to a pile portion or a base cloth. Patent Document 2 discloses a fibrous structure, such as, e.g., a curtain, a carpet and a vehicle interior material in which a composite oxide containing titanium and silicon and a hydrazide compound are adhered to the fiber surface with a resin. Patent Document 3 discloses an odor eliminating carpet in which hydrazine derivative and photocatalyst are adhered to the surface fiber layer with a resin and coconut activated carbon and hydrazine derivative are mixed in a backing resin layer.
Patent Document 1: JP H11-46965, A
Patent Document 2: JP 2003-336170, A
Patent Document 3: JP 2005-198684, A

DISCLOSURE OF THE INVENTION

Problems to be Solved by the Invention

In the meantime, as living odors in a room, there are various types of odors of gases, such as, e.g., basic gases (e.g., ammonia gas, trimethylamine gases), acidic gases (e.g., acetic acid gases), neutral gases (e.g., acetaldehyde gases, formaldehyde gases), sulphur series gases (e.g., hydrogen sulfide gases, mercaptan series gases). None of the aforementioned conventional odor eliminating clothes could effectively eliminate all of four types of gases (basic gases, acidic gases, neutral gases, and sulphur series gases).

The present invention was made in view of the aforementioned technical background, and aims to provide an odor eliminating cloth capable of effectively eliminating any types of odors of, for example, basic gases, acidic gases, neutral gases, sulphur series gases contained in the air of a room, and to provide a manufacturing method thereof.

Means for Solving the Problems

In order to attain the aforementioned objects, the present invention provides the following means.

[1] An odor eliminating cloth, comprising:
an odor eliminating composition containing a porous inorganic substance, a metallic oxide, and an inorganic silicon compound carrying a polyamine compound;
a binder resin; and
a cloth,
wherein the odor eliminating composition is bonded to at least a part of the cloth by means of the binder resin.

[2] The odor eliminating cloth as recited in the aforementioned Item 1, wherein the odor eliminating composition further contains hydrazine derivative.

[3] The odor eliminating cloth as recited in the aforementioned Item 1 or 2, wherein the odor eliminating composition further contains metal hydroxide.

[4] The odor eliminating cloth as recited in any one of the aforementioned Items 1 to 3, wherein an average grain diameter of each odor eliminating component constituting the odor eliminating composition falls within a range of 10 nm to 100 μm.

[5] The odor eliminating cloth as recited in any one of the aforementioned Items 1 to 4, wherein an adhered amount of the odor eliminating composition is 2 to 50 g/m$^2$.

[6] The odor eliminating cloth as recited in any one of the aforementioned Items 1 to 5, wherein the odor eliminating cloth is used as a chair covering cloth, a curtain, a carpet, a wallpaper, or a vehicle interior material.

[7] A method of manufacturing an odor eliminating cloth, comprising:
applying an aqueous solution of pH 6 to 8 containing: a binder resin; and an odor eliminating composition containing a porous inorganic substance, a metallic oxide, and an inorganic silicon compound carrying a polyamine compound to at least a part of a cloth; and thereafter drying the cloth.

[8] The method of manufacturing an odor eliminating cloth as recited in the aforementioned Item 7, wherein the aqueous solution of pH 6 to 8 is applied to at least a part of the cloth having a surface of pH 6 to 8.

[9] The method of manufacturing an odor eliminating cloth as recited in the aforementioned Item 7 or 8, wherein the odor eliminating composition further contains hydrazine derivative.

[10] The method of manufacturing an odor eliminating cloth as recited in any one of the aforementioned Items 7 to 9, wherein the odor eliminating composition further contains metal hydroxide.

Effects of the Invention

In the invention [1], since a porous inorganic substance, a metallic oxide, and an inorganic silicon compound carrying a polyamine compound is given to at least a part of a cloth, any types of odors of basic gases (e.g., ammonia gas, trimethylamine gases), acidic gases (e.g., acetic acid gases), neutral gases (e.g., acetaldehyde gases, formaldehyde gases), and sulphur series gases (e.g., hydrogen sulfide gases, mercaptan series gases) contained, for example, in the air of a room can be effectively eliminated.

In the invention [2], since hydrazine derivative is further given to at least a part of the cloth, there is a merit that the efficiency of eliminating an odor of natural gases, such as, e.g., acetaldehyde gases and formaldehyde gases can be further improved.

In the invention [3], since metal hydroxide is further given to at least a part of the cloth, there is a merit that the efficiency of eliminating an odor of acidic gases, such as, e.g., acetic acid gases, can be further improved.

In the invention [4], since an average grain diameter of each odor eliminating component constituting the odor eliminating composition falls within a range of 10 nm to 100 µm, drop-off of each odor eliminating composition from the cloth can be prevented sufficiently, and the odor elimination effect can be further improved.

In the invention [5], since the adhered amount of the odor eliminating composition is 2 to 50 g/m$^2$, the odor elimination effect can be further improved while keeping a lid on cost.

In the invention [6], a chair covering cloth, a curtain, a carpet, a wallpaper, or a vehicle interior material capable of effectively eliminating any types of odors of basic gases, acidic gases, neutral gases, and sulphur series gases contained in the air of a room can be provided.

In the invention [7] (manufacturing method), since an aqueous solution of pH 6 to 8 containing an odor eliminating composition is applied to at least a part of a cloth, an odor eliminating cloth capable of effectively eliminating any types of odors of basic gases (e.g., ammonia gases, trimethylamine gases), acidic gases (e.g., acetic acid gases), neutral gases (e.g., acetaldehyde gases, formaldehyde gases), and sulphur series gases (e.g., hydrogen sulfide gases, mercaptan series gases) contained, for example, in the air of a room can be manufactured. Using an aqueous solution having a pH value exceeding 8 tends to results in deteriorated performance of eliminating odors of basic gases. On the other hand, using an aqueous solution having a pH value less than 6 causes deteriorated performance of eliminating odors of sulphur series gases and acidic gases.

In the invention [8], since the pH of the surface of the cloth to be treated by the aqueous solution is 6 to 8, an odor eliminating cloth capable of effectively eliminating any types of odors of basic gases, acidic gases, neutral gases, and sulphur series gases contained, for example, in the air of a room can be provided assuredly.

In the invention [9], since the odor eliminating composition further contains hydrazine derivative, an odor eliminating cloth further improved in the efficiency of eliminating odors of natural gases, such as, e.g., acetaldehyde gases and formaldehyde gases, can be further improved.

In the invention [10], since the odor eliminating composition further contains metal hydroxide, an odor eliminating cloth further improved in the odor elimination effect of eliminating acidic gases, such as, e.g., acetic acid gases can be manufactured.

BRIEF DESCRIPTION OF THE DRAWINGS

FIG. 1 is a cross-sectional view showing an embodiment of an odor eliminating cloth according to this invention.

DESCRIPTION OF REFERENCE NUMERALS

1 . . . odor eliminating cloth
2 . . . pile layer
3 . . . base cloth
4 . . . backing layer

BEST MODE FOR CARRYING OUT THE INVENTION

An odor eliminating cloth according to this invention is characterized in that an odor eliminating composition containing (a) a porous inorganic substance, (b) a metallic oxide, and (c) an inorganic silicon compound carrying a polyamine compound is fixed to at least a part of a cloth by means of a binder resin.

In the aforementioned cloth, since three components of (a), (b) and (c) are given to at least a part of the cloth, any types of odors of basic gases (e.g., ammonia gas, trimethylamine gases), acidic gases (e.g., acetic acid gases), neutral gases (e.g., acetaldehyde gases, formaldehyde gases), and sulphur series gases (e.g., hydrogen sulfide gases, mercaptan series gases) contained, for example, in the air of a room, can be effectively eliminated.

The porous inorganic substance is porous and therefore large in the surface area, which exerts excellent odor absorbing performance. The porous inorganic substance is not specifically limited, but can be exemplified by, for example, activated carbon, zeolite, silica gel, and Bakuhanseki (Barley-rice stone). Among other things, it is preferable to use zeolite which exerts excellent performance of absorbing acetic acid, ammonia, and the like. Zeolite is white in color and has less effect on the color of a cloth when adhered to the cloth. From this view point, zeolite can be preferably used.

The metallic oxide is not specifically limited, but can be exemplified by, for example, alumina, titanium oxide, zinc oxide, and ferric oxide. This metallic oxide functions mainly as photocatalyst and executes oxidative decomposition of organic matters with its strong oxidizing power.

The inorganic silicon compound carrying a polyamine compound is not specifically limited, but can be exemplified by, for example, porous silicon dioxide carrying a polyamine compound and aluminum silicate carrying a polyamine compound.

The polyamine compound is not specifically limited, but can be exemplified by, for example, aliphatic polyamine, aromatic polyamine and alicyclic polyamine. Concretely, for example, diethylene triamine, and tetraethylenepentamine can be exemplified.

The method of carrying a polyamine compound on an inorganic silicon compound is not specifically limited, but can be exemplified by, for example, a method comprising: creating an aqueous solution of a polyamine compound; immersing an inorganic silicon compound in the aqueous solution; and thereafter heat burning the inorganic silicon compound taken out of the aqueous solution to thereby obtain the inorganic silicon compound carrying a polyamine compound.

The polyamine compound is effective for eliminating odors of aldehyde gases, and the inorganic silicon compound is effective for eliminating odors of basic gases. By using a porous inorganic substance and a metallic oxide in combination with the polyamine compound and the inorganic silicon compound, various odors in contact with the odor eliminating cloth can be effectively eliminated.

The odor eliminating composition preferably contains (d) hydrazine derivative in addition to (a) a porous inorganic substance, (b) a metallic oxide, and (c) an inorganic silicon compound carrying a polyamine compound. The hydrazine derivative adhered to a cloth can further improve the efficiency of eliminating odors of natural gases, such as, e.g., acetaldehyde gases and formaldehyde gases. Using such hydrazine derivative causes a chemical reaction of, e.g., aldehyde series to exert excellent odor absorbing performance, resulting in further improved excellent odor elimination performance.

The hydrazine derivative can be exemplified by, for example, a reaction product obtained by reacting a hydrazine series compound with a long-chain aliphatic series compound, and a reaction product obtained by reacting a hydrazine series compound with an aromatic series compound.

Among other things, it is preferable to use a reaction product of one or two compounds selected from the group consisting of hydrazine and semicarbazide and one or two or more compounds selected from the group consisting of monocarbonic acid, dicarboxylic acid, aromatic monocarbonic acid, and aromatic dicarboxylic acid having a carbon number of 8 to 16, or a reaction product of one or two compounds selected from the group consisting of hydrazine and semicarbazide and one or two or more compounds selected from the group consisting of a monoglycidyl derivative and a diglycidyl derivative having the carbon number of 8 to 16. The reaction product can be concretely exemplified by, for example, dihydrazide sebacate, dihydrazide dodecanedioic acid, and dihydrazide isophthalic acid, but not limited to these exemplified compounds. The solubility of the hydrazine derivative to water is preferably 5 g/L or less at a temperature of 25° C. In cases where the hydrazine derivative has low-water solubility falling within this range, the hydrazine derivative can be prevented from being resolved in water and flowing out of the cloth even if the hydrazine derivative comes into contact with water at the time of washing.

The odor eliminating composition preferably contains (e) metal hydroxide in addition to (a) a porous inorganic substance, (b) a metallic oxide, and (c) an inorganic silicon compound carrying a polyamine compound. The metal hydroxide adhered to a cloth can further improve the efficiency of eliminating odors of acidic gases, such as, e.g., acetic acid gases.

The metallic hydroxide is not specifically limited, but can be exemplified by, for example, zirconium hydroxide, aluminum hydroxide, magnesium hydroxide, ferrous hydroxide, and copper hydroxide. Among other things, from the viewpoint of the most excellent efficiency of eliminating odors of acetic acid gases, zirconium hydroxide is preferably used.

It is preferable that the average grain diameter of each odor eliminating component (porous inorganic substance/metallic oxide/inorganic silicon compound carrying a polyamine compound/hydrazine derivative/metallic hydroxide) constituting the odor eliminating composition falls within the range of 10 nm to 100 μm. When the grain diameter falls within this range, these substances does not cause surface roughness when they are carried by a cloth. It is especially preferable that the average grain diameter of each odor eliminating component constituting the odor eliminating composition falls within the range of 10 nm to 10 μm, more preferably 10 nm to 5 μm.

The adhered amount (not including the binder resin) of the odor eliminating composition is preferably set to 2 to 50 g/m$^2$ (dry mass). If it is less than 2 g/m$^2$, it becomes difficult to attain sufficient odor elimination performance. Thus, it is not preferable. On the other hand, even if it exceeds 50 g/m$^2$, the odor elimination performance will not be further improved, resulting in increased cost. Thus, it is not preferable.

As the binder resin, any resin can be used. The binder resin can be exemplified by, for example, self-linking type acrylic resin, metaacrylic resin, urethane resin, silicon resin, glyoxal resin, polyvinyl acetate resin, vinylidene chloride resin, butadiene resin, melamine resin, epoxy resin, acrylic-silicon copolymer resin, ethylene-vinyl acetate copolymer resin, isobutylene-maleic anhydride copolymer resin, and ethylene-styrene-acrylate-metaacrylate copolymer resin. Two or more of these resins can be mixed into a binder resin.

It is preferable that the adhered amount (not including the odor eliminating composition) of the binder resin is set to 0.5 to 50 g/m$^2$ (dry mass). The fixed amount ratio (dry mass ratio) of the odor eliminating composition/the binder resin is preferably set so as to fall within the range of 1/1 to 4/1.

The mixing mass ratio of each odor eliminating component in the odor eliminating composition is not specifically limited, but is preferably set so that the metallic oxide falls within the range of 20 to 1,000 mass parts and the inorganic silicon compound carrying a polyamine compound falls within the range of 20 to 1,000 mass parts, with respect to a porous inorganic substance of 100 mass parts. In the structure containing hydrazine derivative, it is preferable that the metallic oxide falls within the range of 20 to 1,000 mass parts, the inorganic silicon compound carrying a polyamine compound falls within the range of 20 to 900 mass parts, and the hydrazine derivative falls within the range of 50 to 500 mass parts, with respect to a porous inorganic substance of 100 mass parts. Furthermore, in the structure containing metallic hydroxide, it is preferable that the metallic oxide falls within the range of 20 to 1,000 mass parts, the inorganic silicon compound carrying a polyamine compound falls within the range of 20 to 1,000 mass parts, and the metallic hydroxide falls within the range of 10 to 500 mass parts, with respect to a porous inorganic substance of 100 mass parts.

In the odor eliminating cloth 1 of this invention, the portion to which the odor eliminating composition is to be applied is not specifically limited, and can be, for example, the entirety of the cloth or the part thereof. In the case of a carpet, the odor eliminating composition can be fixed to the pile yarn 2, the base cloth 3 (see FIG. 1), or the resin constituting the sealing layer formed on the rear surface of the base cloth.

Next, the method of manufacturing the odor eliminating cloth according to this invention will be explained. This manufacturing method is characterized in that an aqueous solution of pH 6 to 8 containing the odor eliminating composition and the binder resin is applied to at least a part of a cloth and then dried. This odor eliminating composition contains (a) a porous inorganic substance, (b) a metallic oxide, and (c) an inorganic silicon compound carrying a polyamine compound, and preferably further contains (d) hydrazine derivative and/or (e) metal hydroxide.

In this manufacturing method, the pH value of the aqueous solution containing the odor eliminating composition and the binder resin is set so as to fall within the range of 6 to 8. Therefore, an odor eliminating cloth capable of effectively eliminating any types of odors of basic gases, acidic gases, neutral gases, sulphur series gases contained in, for example, the air of a room can be provided. Using an aqueous solution having a pH value exceeding 8 tends to results in deteriorated performance of eliminating odors of basic gases. On the other hand, using an aqueous solution having a pH value less than 6 causes deteriorated performance of eliminating odors of sulphur series gases and acidic gases.

In adjusting the pH value of the aqueous solution so as to fall within the range of 6 to 8, pH adjuster, such as, e.g., acid and base, is usually added. Such pH adjuster is not specifically limited, but can be exemplified by, for example, citric acid, sulfuric acid, hydrochloric acid, sodium carbonate, sodium hydroxide, and potassium hydroxide.

At the time of adjusting the aqueous solution, it is preferable to sufficiently disperse each odor eliminating component of the odor eliminating composition into water and form a binder resin emulsion. The mixing order at the time of adjusting the aqueous solution is not specifically limited, but it is preferable that each odor eliminating component of the odor eliminating composition is previously dispersed in water, and then a binder resin is mixed thereto since each odor eliminating component of the odor eliminating composition and the binder resin can be evenly dispersed with water.

The aqueous solution can further contain various additives, such as, e.g., dispersant and thickener, in addition to the odor eliminating composition and the binder resin.

The application method of applying the aqueous solution to a cloth is not specifically limited, but can be exemplified by, for example, a spraying method, an immersion method, a coating method and a padding method. The aqueous solution applying portion of a cloth is not specifically limited, and the aqueous solution can be applied to, for example, the entirety of the cloth or the part thereof. In the case of a carpet, the aqueous solution can be applied to the pile yarn 2, the base cloth 3, or the backing layer 4 (see FIG. 1). Furthermore, the aqueous solution can be applied to the surface skin layer in which piles 2 are implanted in the base fabric 3 or can be applied to the integrated layer in which a surface skin layer and a backing layer are integrally laminated via an adhesive layer. In the case of a curtain, the aqueous solution can be applied to a raw curtain cloth or to a sewn curtain cloth.

The cloth is dried after the application of the aqueous solution. This drying process is preferably performed by a heat treatment. This heat treatment temperature is preferably set to 100 to 180° C. The heat treatment within this temperature range can enhance the fixing performance of the odor eliminating composition, which in turn can further improve the continuous durability of the odor eliminating performance.

In general, a cloth is subjected to, other than a process treatment for giving an odor eliminating function, various process treatments for giving various functions, such as, e.g., a fire retardant function, a moth-proof function, and an anti-soil function. In this case, depending on the process treatment, the pH value of the cloth surface becomes the acidic side or the basic side, resulting in insufficient odor eliminating effects in some cases. Accordingly, in this manufacturing method, as a cloth to which the aqueous solution is applied, a cloth having a surface of pH 6 to 8 is used. If the pH of the cloth surface exceeds 8, the odor elimination ratio for eliminating basic gases deteriorates. On the other hand, if the pH of the cloth surface is less than 6, the odor elimination ratio for eliminating sulphur series gases and acidic gases deteriorates.

Thus, it is important that the pH value of the surface of the cloth (cloth before the odor elimination treatment) to which the aqueous solution is applied falls within the range of 6 to 8. The adjustment of the pH value of the cloth surface can be performed by, for example, a neutralization treatment in which the cloth is immersed in an aqueous solution of, for example, phosphate or citric acid.

The aforementioned "pH of the cloth surface" is a value measured as follows. That is, it is a value obtained by dropping distilled water 0.2 g (pH 6.88) from which any remaining air was fully expelled by nitrogen on the cloth surface, leaving this state for 1 to 5 minutes, and thereafter measuring the pH of the water on the cloth surface.

In this invention, the cloth is not specifically limited, but can be exemplified by, for example, woven fabric, knit fabric, nonwoven fabric, and yarn-standing cloth (e.g., tufted carpet, moquette). The concrete application thereof is not specifically limited, but can be exemplified by, for example, a chair covering cloth, a curtain, a carpet, a wallpaper, and a vehicle interior material (railroad vehicle interior material, automobile interior material, or aircraft interior material). It is preferable that the cloth has such air permeability that odors contained in natural convection room air can sufficiently contact with the odor eliminating composition fixed to the cloth.

The fibers constituting the cloth are not specifically limited, but can be exemplified by, for example, natural fibers, such as, e.g., hemp, cotton, and wool, as well as polyester fibers, polyamide fibers, polypropylene fibers, acrylic fibers, and rayon fibers.

EXAMPLES

Concrete examples of this invention will be explained below. However, it should be noted that this invention is not specifically limited to these examples.

Example 1

A polyester curtain cloth (weight per unit area: 435 g/m$^2$, cloth surface pH: 5.0) to which a fire retardant treatment was performed using guanidine phosphate was subjected to a neutralization treatment in a sodium phosphate solution, and then dried. Thus, a fire retardant curtain material (cloth) having a surface of pH 7.0 was obtained.

On the other hand, 0.5 mass parts of dihydrazide sebacate having an average grain diameter of 1 μm, 1.5 mass parts of zeolite having an average grain diameter of 5 μm, 2.5 mass parts of zinc oxide having an average grain diameter of 10 nm, and 1.5 mass parts of silicon dioxide having an average grain diameter of 10 μm carrying diethylene triamine were added to 84 mass parts of water, and then agitated using an agitation device. Thus, an aqueous solution in which each particle was dispersed evenly was obtained. After adding 10 mass parts of acrylic silicon series binder resin (solid content: 50 mass %) to the aforementioned aqueous solution, a citric acid solution was gradually added by monitoring a pH meter while agitating using the agitation device. Thus, an aqueous dispersion liquid (treatment aqueous solution) in which the pH was adjusted to 7.0 was obtained.

Next, after immersing the fire retardant curtain material in the aforementioned treatment aqueous solution, the material was taken out and squeezed with a mangle and then dried at 130° C. for 15 minutes. Thus, an odor eliminating curtain (odor eliminating cloth) was obtained. The adhered amount of each odor eliminating component was as follows: dihydrazide sebacate: 0.5 g/m$^2$, zeolite: 1.5 g/m$^2$, zinc oxide: 2.5 g/m$^2$, silicon dioxide carrying diethylene triamine: 1.5 g/m$^2$.

Example 2

A polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried. Thus, a fire retardant curtain material (cloth) having a surface of pH 7.0 was obtained.

On the other hand, 4.0 mass parts of dihydrazide sebacate having an average grain diameter of 2 μm, 2.0 mass parts of zeolite having an average grain diameter of 10 μm, 2.0 mass parts of zinc oxide having an average grain diameter of 10 nm, and 2.0 mass parts of silicon dioxide having an average grain diameter of 10 μm carrying diethylene triamine were added to 80 mass parts of water, and then agitated using an agitation device. Thus, an aqueous solution in which each particle was dispersed evenly was obtained. After adding 10 mass parts of acrylic silicon series binder resin (solid content: 50 mass %) to the aforementioned aqueous solution, a citric acid solution was gradually added by monitoring a pH meter while agitating using the agitation device. Thus, an aqueous dispersion liquid (treatment aqueous solution) in which the pH was adjusted to 7.0 was obtained.

Next, after immersing the fire retardant curtain material in the aforementioned treatment aqueous solution, the material was taken out and squeezed with a mangle and then dried at 130° C. for 15 minutes. Thus, an odor eliminating curtain (odor eliminating cloth) was obtained. The adhered amount of each odor eliminating component was as follows: dihydrazide sebacate: 4.0 g/m$^2$, zeolite: 2.0 g/m$^2$, zinc oxide: 2.0 g/m$^2$, silicon dioxide carrying diethylene triamine: 2.0 g/m$^2$.

Example 3

A polyester curtain cloth (weight per unit area: 95 g/m$^2$, cloth surface pH: 5.0) to which a fire retardant treatment was performed using guanidine phosphate was subjected to a neutralization treatment in a disodium phosphate solution, and then dried. Thus, a fire retardant curtain material (cloth) having a surface of pH 7.0 was obtained.

On the other hand, 4.0 mass parts of dihydrazide sebacate having an average grain diameter of 2 μm, 3.0 mass parts of zeolite having an average grain diameter of 5 μm, 5.0 mass parts of zinc oxide having an average grain diameter of 10 nm, and 4.0 mass parts of silicon dioxide having an average grain diameter of 10 μm carrying diethylene triamine were added to 74 mass parts of water, and then agitated using an agitation device. Thus, an aqueous solution in which each particle was dispersed evenly was obtained. After adding 10 mass parts of acrylic silicon series binder resin (solid content: 50 mass %) to the aforementioned aqueous solution, a citric acid solution was gradually added by monitoring a pH meter while agitating using the agitation device. Thus, an aqueous dispersion liquid (treatment aqueous solution) in which the pH was adjusted to 7.0 was obtained.

Next, after immersing the fire retardant curtain material in the aforementioned treatment aqueous solution, the material was taken out and squeezed with a mangle and then dried at 130° C. for 15 minutes. Thus, an odor eliminating curtain (odor eliminating cloth) was obtained. The adhered amount of each odor eliminating component was as follows: dihydrazide sebacate: 4.0 g/m$^2$, zeolite: 3.0 g/m$^2$, zinc oxide: 5.0 g/m$^2$, silicon dioxide carrying diethylene triamine: 4.0 g/m$^2$.

Example 4

A polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried. Thus, a fire retardant curtain material (cloth) having a surface of pH 7.0 was obtained.

On the other hand, 0.5 mass parts of dihydrazide dodecanedioic acid having an average grain diameter of 3 μm, 1.5 mass parts of silica having an average grain diameter of 3 μm, 2.5 mass parts of titanium oxide having an average grain diameter of 10 nm, and 1.5 mass parts of silicon dioxide having an average grain diameter of 10 μm carrying diethylene triamine were added to 84 mass parts of water, and then agitated using an agitation device. Thus, an aqueous solution in which each particle was dispersed evenly was obtained. After adding 10 mass parts of acrylic silicon series binder resin (solid content: 50 mass %) to the aforementioned aqueous solution, a citric acid solution was gradually added by monitoring a pH meter while agitating using the agitation device. Thus, an aqueous dispersion liquid (treatment aqueous solution) in which the pH was adjusted to 7.0) was obtained.

Next, after immersing the fire retardant curtain material in the aforementioned treatment aqueous solution, the material was taken out and squeezed with a mangle and then dried at 130° C. for 15 minutes. Thus, an odor eliminating curtain (odor eliminating cloth) was obtained. The adhered amount of each odor eliminating component was as follows: dihydrazide dodecanedioic acid: 0.5 g/m$^2$, silica: 1.5 g/m$^2$, titanium oxide: 2.5 g/m$^2$, silicon dioxide carrying diethylene triamine: 1.5 g/m$^2$.

Example 5

An odor eliminating curtain was obtained in the same manner as in Example 1 except that dihydrazide sebacate was not added to a treatment aqueous solution at all.

Example 6

An odor eliminating curtain was obtained in the same manner as in Example 1 except that a polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried to thereby obtain a fire retardant curtain having a surface of pH 6.3.

Example 7

An odor eliminating curtain was obtained in the same manner as in Example 1 except that a polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried to thereby obtain a fire retardant curtain having a surface of pH 7.7.

Example 8

An odor eliminating curtain was obtained in the same manner as in Example 1 except that a treatment aqueous solution in which the pH value was adjusted to 6.2 was used.

Example 9

An odor eliminating curtain was obtained in the same manner as in Example 1 except that a treatment aqueous solution in which the pH value was adjusted to 7.9 was used.

Comparative Example 1

An odor eliminating curtain was obtained in the same manner as in Example 1 except that a polyester curtain cloth (weight per unit area: 435 g/m², cloth surface pH: 5.0) to which a fire retardant treatment was performed using guanidine phosphate was not subjected to a neutralization treatment was used as it is (a fire retardant curtain having a surface of pH 5.0).

Comparative Example 2

An odor eliminating curtain was obtained in the same manner as in Example 1 except that no zinc oxide was added to a treatment aqueous solution.

Comparative Example 3

An odor eliminating curtain was obtained in the same manner as in Example 1 except that a polyester curtain cloth (weight per unit area: 435 g/m², cloth surface pH: 5.0) to which a fire retardant treatment was performed using guanidine phosphate was not subjected to a neutralization treatment was used as it is (a fire retardant curtain having a surface of pH 5.0) and the adhered amount of each odor elimination component was set as shown in Table 1.

Comparative Example 4

An odor eliminating curtain was obtained in the same manner as in Example 1 except that no silicon dioxide carrying diethylene triamine was added to a treatment aqueous solution.

Comparative Example 5

An odor eliminating curtain was obtained in the same manner as in Example 1 except that no zeolite was added to a treatment aqueous solution.

Comparative Example 6

An odor eliminating curtain was obtained in the same manner as in Example 1 except that a polyester curtain cloth (weight per unit area: 435 g/m², cloth surface pH: 5.0) to which a fire retardant treatment was performed using guanidine phosphate was subjected to a neutralization treatment in a disodium phosphate solution, and then dried to thereby obtain a fire retardant curtain having a surface of pH 9.0.

Comparative Example 7

An odor eliminating curtain was obtained in the same manner as in Example 1 except that a treatment aqueous solution in which the pH value was adjusted to 5.0 was used.

Comparative Example 8

An odor eliminating curtain was obtained in the same manner as in Example 1 except that a treatment aqueous solution in which the pH value was adjusted to 8.5 was used.

TABLE 1

| | Odor elimination component adhered amount (g/m²) | | | | | | | | |
|---|---|---|---|---|---|---|---|---|---|
| | Hydrazine derivative | | Porous inorganic substance | | Metallic oxide | | Silicon dioxide carrying diethylene triamine | pH of treatment aqueous solution | Surface pH of pre-treatment cloth |
| | Dihydrazide sebacate | Dihydrazide dodecanedioic acid | Zeolite | Silica | Zinc oxide | Titanium oxide | | | |
| Ex. 1 | 0.5 | — | 1.5 | — | 2.5 | — | 1.5 | 7.0 | 7.0 |
| Ex. 2 | 4.0 | — | 2.0 | — | 2.0 | — | 2.0 | 7.0 | 7.0 |
| Ex. 3 | 4.0 | — | 3.0 | — | 5.0 | — | 4.0 | 7.0 | 7.0 |
| Ex. 4 | — | 0.5 | — | 1.5 | — | 2.5 | 1.5 | 7.0 | 7.0 |
| Ex. 5 | — | — | 1.5 | — | 2.5 | — | 1.5 | 7.0 | 7.0 |
| Ex. 6 | 0.5 | — | 1.5 | — | 2.5 | — | 1.5 | 7.0 | 6.3 |
| Ex. 7 | 0.5 | — | 1.5 | — | 2.5 | — | 1.5 | 7.0 | 7.7 |
| Ex. 8 | 0.5 | — | 1.5 | — | 2.5 | — | 1.5 | 6.2 | 7.0 |
| Ex. 9 | 0.5 | — | 1.5 | — | 2.5 | — | 1.5 | 7.9 | 7.0 |
| Comp. Ex. 1 | 0.5 | — | 1.5 | — | 2.5 | — | 1.5 | 7.0 | 5.0 |
| Comp. Ex. 2 | 0.5 | — | 1.5 | — | — | — | 1.5 | 7.0 | 7.0 |
| Comp. Ex. 3 | 1.5 | — | 4.5 | — | 7.5 | — | 4.5 | 7.0 | 5.0 |
| Comp. Ex. 4 | 0.5 | — | 1.5 | — | 2.5 | — | — | 7.0 | 7.0 |
| Comp. Ex. 5 | — | — | — | — | 2.5 | — | 1.5 | 7.0 | 7.0 |
| Comp. Ex. 6 | 0.5 | — | 1.5 | — | 2.5 | — | 1.5 | 7.0 | 9.0 |
| Comp. Ex. 7 | 0.5 | — | 1.5 | — | 2.5 | — | 1.5 | 5.0 | 7.0 |
| Comp. Ex. 8 | 0.5 | — | 1.5 | — | 2.5 | — | 1.5 | 8.5 | 7.0 |

TABLE 2

| | Odor elimination performance test results | | | | | | |
|---|---|---|---|---|---|---|---|
| | Acetic acid | Hydrogen sulfide | Methyl mercaptan | Ammonia | Trimethyl amine | Formaldehyde | Acetaldehyde |
| Ex. 1 | ○ | ◎ | ◎ | ◎ | ◎ | ◎ | ◎ |
| Ex. 2 | ○ | ◎ | ◎ | ◎ | ◎ | ◎ | ◎ |
| Ex. 3 | ◎ | ◎ | ◎ | ◎ | ◎ | ◎ | ◎ |
| Ex. 4 | ○ | ○ | ○ | ◎ | ◎ | ◎ | ◎ |
| Ex. 5 | ○ | ◎ | ◎ | ◎ | ◎ | ○ | ◎ |

TABLE 2-continued

<Odor elimination performance test results>

|  | Acetic acid | Hydrogen sulfide | Methyl mercaptan | Ammonia | Trimethy amine | Formaldehyde | Acetaldehyde |
|---|---|---|---|---|---|---|---|
| Ex. 6 | ○ | ◎ | ◎ | ◎ | ◎ | ○ | ◎ |
| Ex. 7 | ○ | ◎ | ◎ | ◎ | ◎ | ◎ | ◎ |
| Ex. 8 | ○ | ◎ | ◎ | ◎ | ◎ | ◎ | ◎ |
| Ex. 9 | ○ | ◎ | ◎ | ○ | ◎ | ◎ | ◎ |
| Comp. Ex. 1 | Δ | X | X | ◎ | ◎ | ◎ | ◎ |
| Comp. Ex. 2 | ○ | X | X | ○ | Δ | ◎ | ◎ |
| Comp. Ex. 3 | ○ | X | X | ◎ | ◎ | ◎ | ◎ |
| Comp. Ex. 4 | ○ | ◎ | ◎ | ○ | ◎ | Δ | X |
| Comp. Ex. 5 | ○ | Δ | Δ | ○ | Δ | ◎ | ◎ |
| Comp. Ex. 6 | ◎ | ◎ | ◎ | X | X | ◎ | ◎ |
| Comp. Ex. 7 | Δ | X | X | ◎ | ◎ | ◎ | ◎ |
| Comp. Ex. 8 | ◎ | ◎ | ◎ | X | X | Δ | X |

Example 10

A polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried. Thus, a fire retardant curtain material (cloth) having a surface of pH 7.0 was obtained.

On the other hand, 1.0 mass parts of zirconium hydroxide having an average grain diameter of 3 μm, 2.0 mass parts of zeolite having an average grain diameter of 5 μm, 3.0 mass parts of zinc oxide having an average grain diameter of 10 nm, and 2.0 mass parts of silicon dioxide having an average grain diameter of 10 μm carrying diethylene triamine were added to 82 mass parts of water, and then agitated using an agitation device. Thus, an aqueous solution in which each particle was dispersed evenly was obtained. After adding 10 mass parts of acrylic silicon series binder resin (solid content: 50 mass %) to the aforementioned aqueous solution, a citric acid solution was gradually added by monitoring a pH meter while agitating. Thus, an aqueous dispersion liquid (treatment aqueous solution) in which the pH was adjusted to 6.8 was obtained.

Next, after immersing the fire retardant curtain material in the aforementioned treatment aqueous solution, the material was taken out and squeezed with a mangle and then dried at 130° C. for 15 minutes. Thus, an odor eliminating curtain (odor eliminating cloth) was obtained. The adhered amount of each odor eliminating component was as follows: zirconium hydroxide: 1.0 g/m$^2$, zeolite: 2.0 g/m$^2$, zinc oxide: 3.0 g/m$^2$, silicon dioxide carrying diethylene triamine: 2.0 g/m$^2$.

Example 11

An odor eliminating curtain was obtained in the same manner as in Example 10 except that zeolite having an average grain diameter 10 μm was used and that the adhered amount of each odor eliminated amount was set as shown in Table 3.

Example 12

An odor eliminating curtain was obtained in the same manner as in Example 10 except that a fire retardant carpet having a surface of pH 7.0 was used in place of the curtain material was used and the adhered amount of each odor eliminated amount was set as shown in Table 3.

Example 13

An odor eliminating chair covering cloth (seat fabric) was obtained in the same manner as in Example 10 except that a seat fabric having a surface of pH 7.0 was used in place of the curtain material was used.

Example 14

An odor eliminating curtain was obtained in the same manner as in Example 10 except that a wallpaper having a surface of pH 7.0 was used in place of the curtain material was used and the adhered amount of each odor eliminated amount was set as shown in Table 3.

Example 15

A polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried. Thus, a fire retardant curtain material (cloth) having a surface of pH 7.0 was obtained.

On the other hand, 1.0 mass parts of magnesium hydroxide having an average grain diameter of 10 μm, 2.0 mass parts of silica having an average grain diameter of 3 μm, 3.0 mass parts of titanium oxide having an average grain diameter of 10 nm, and 2.0 mass parts of silicon dioxide having an average grain diameter of 10 μm carrying diethylene triamine were added to 82 mass parts of water, and then agitated using an agitation device. Thus, an aqueous solution in which each particle was dispersed evenly was obtained. After adding 10 mass parts of acrylic silicon series binder resin (solid content: 50 mass %) to the aforementioned aqueous solution, a citric acid solution was gradually added by monitoring a pH meter while agitating using an agitation device. Thus, an aqueous dispersion liquid (treatment aqueous solution) in which the pH was adjusted to 6.8 was obtained.

Next, after immersing the fire retardant curtain material in the aforementioned treatment aqueous solution, the material was taken out and squeezed with a mangle and then dried at 130° C. for 15 minutes. Thus, an odor eliminating curtain (odor eliminating cloth) was obtained. The adhered amount of each odor eliminating component was as follows: magnesium hydroxide: 1.0 g/m$^2$, silica: 2.0 g/m$^2$, titanium oxide: 3.0 g/m$^2$, silicon dioxide carrying diethylene triamine: 2.0 g/m$^2$.

Example 16

An odor eliminating curtain was obtained in the same manner as in Example 10 except that zirconium hydroxide was not added to a treatment aqueous solution at all.

Example 17

An odor eliminating curtain was obtained in the same manner as in Example 10 except that a polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried to thereby obtain a fire retardant curtain having a surface of pH 6.2.

Example 18

An odor eliminating curtain was obtained in the same manner as in Example 10 except that a polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried to thereby obtain a fire retardant curtain having a surface of pH 7.8.

Example 19

An odor eliminating curtain was obtained in the same manner as in Example 10 except that the treatment aqueous solution was adjusted to pH 6.4.

Example 20

An odor eliminating curtain was obtained in the same manner as in Example 1 except that the treatment aqueous solution was adjusted to pH 7.6.

Comparative Example 9

An odor eliminating curtain was obtained in the same manner as in Example 10 except that no zeolite was added to a treatment aqueous solution.

Comparative Example 10

An odor eliminating curtain was obtained in the same manner as in Example 10 except that no zinc oxide was added to a treatment aqueous solution.

Comparative Example 11

An odor eliminating curtain was obtained in the same manner as in Example 10 except that no silicon dioxide carrying diethylene triamine was added to a treatment aqueous solution.

Comparative Example 12

An odor eliminating curtain was obtained in the same manner as in Example 10 except that a polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried to thereby obtain a fire retardant curtain having a surface of pH 5.1.

Comparative Example 13

An odor eliminating curtain was obtained in the same manner as in Example 10 except that a polyester curtain cloth (weight per unit area: 435 g/m$^2$, cloth surface pH: 5.0) to which a fire retardant treatment was performed using guanidine phosphate was subjected to a neutralization treatment in a disodium phosphate solution, and then dried to thereby obtain a fire retardant curtain having a surface of pH 9.0.

Comparative Example 14

An odor eliminating curtain was obtained in the same manner as in Example 10 except that the treatment aqueous solution was adjusted to pH 5.2.

Comparative Example 15

An odor eliminating curtain was obtained in the same manner as in Example 10 except that the treatment aqueous solution was adjusted to pH 9.0.

Comparative Example 16

An odor eliminating curtain was obtained in the same manner as in Example 10 except that a polyester curtain cloth (weight per unit area: 435 g/m$^2$, cloth surface pH: 5.0) to which a fire retardant treatment was performed using guanidine phosphate was not subjected to a neutralization treatment in a disodium phosphate solution, and then dried to thereby obtain a fire retardant curtain having a surface of pH 5.0.

TABLE 3

| | Odor elimination component adhered amount (g/m$^2$) | | | | | | | |
|---|---|---|---|---|---|---|---|---|
| | Metal hydroxide | | Porous inorganic substance | Metallic oxide | | Silicon dioxide carrying diethylene triamine | pH of treatment aqueous solution | Surface pH of pre-treatment cloth |
| | Zirconium hydroxide | Magnesium hydroxide | Zeolite | Silica | Zinc oxide | Titanium oxide | | | |
| Ex. 10 | 1.0 | — | 2.0 | — | 3.0 | — | 2.0 | 6.8 | 7.0 |
| Ex. 11 | 2.0 | — | 2.0 | — | 2.0 | — | 2.0 | 6.8 | 7.0 |
| Ex. 12 | 4.0 | — | 4.0 | — | 5.0 | — | 4.0 | 6.8 | 7.0 |
| Ex. 13 | 1.0 | — | 2.0 | — | 3.0 | — | 2.0 | 6.8 | 7.0 |
| Ex. 14 | 0.5 | — | 0.5 | — | 1.0 | — | 1.5 | 6.8 | 7.0 |
| Ex. 15 | — | 1.0 | — | 2.0 | — | 3.0 | 2.0 | 6.8 | 7.0 |

TABLE 3-continued

| | Odor elimination component adhered amount (g/m²) | | | | | | pH of treatment aqueous solution | Surface pH of pre-treatment cloth |
|---|---|---|---|---|---|---|---|---|
| | Metal hydroxide | | Porous inorganic substance | | Metallic oxide | | Silicon dioxide carrying diethylene triamine | |
| | Zirconium hydroxide | Magnesium hydroxide | Zeolite | Silica | Zinc oxide | Titanium oxide | | |
| Ex. 16 | — | — | 2.0 | — | 3.0 | — | 2.0 | 6.8 | 7.0 |
| Ex. 17 | 1.0 | — | 2.0 | — | 3.0 | — | 2.0 | 6.8 | 6.2 |
| Ex. 18 | 1.0 | — | 2.0 | — | 3.0 | — | 2.0 | 6.8 | 7.8 |
| Ex. 19 | 1.0 | — | 2.0 | — | 3.0 | — | 2.0 | 6.4 | 7.0 |
| Ex. 20 | 1.0 | — | 2.0 | — | 3.0 | — | 2.0 | 7.6 | 7.0 |
| Comp. Ex. 9 | 1.0 | — | — | — | 3.0 | — | 2.0 | 6.8 | 7.0 |
| Comp. Ex. 10 | 1.0 | — | 2.0 | — | — | — | 2.0 | 6.8 | 7.0 |
| Comp. Ex. 11 | 1.0 | — | 2.0 | — | 3.0 | — | — | 6.8 | 7.0 |
| Comp. Ex. 12 | 1.0 | — | 2.0 | — | 3.0 | — | 2.0 | 6.8 | 5.1 |
| Comp. Ex. 13 | 1.0 | — | 2.0 | — | 3.0 | — | 2.0 | 6.8 | 9.0 |
| Comp. Ex. 14 | 1.0 | — | 2.0 | — | 3.0 | — | 2.0 | 5.2 | 7.0 |
| Comp. Ex. 15 | 1.0 | — | 2.0 | — | 3.0 | — | 2.0 | 9.0 | 7.0 |
| Comp. Ex. 16 | 1.0 | — | 2.0 | — | 3.0 | — | 2.0 | 5.0 | 5.0 |

TABLE 4

<Odor elimination performance test results>

| | Acetic acid | Hydrogen sulfide | Methyl mercaptan | Ammonia | Trimethy amine | Formaldehyde | Acetaldehyde |
|---|---|---|---|---|---|---|---|
| Ex. 10 | ◎ | ◎ | ◎ | ◎ | ◎ | ◎ | ◎ |
| Ex. 11 | ◎ | ◎ | ◎ | ◎ | ◎ | ◎ | ◎ |
| Ex. 12 | ◎ | ◎ | ◎ | ◎ | ◎ | ◎ | ◎ |
| Ex. 13 | ◎ | ◎ | ◎ | ◎ | ◎ | ◎ | ◎ |
| Ex. 14 | ◎ | ○ | ○ | ○ | ○ | ◎ | ◎ |
| Ex. 15 | ○ | ○ | ○ | ◎ | ○ | ○ | ◎ |
| Ex. 16 | ○ | ◎ | ◎ | ◎ | ◎ | ◎ | ◎ |
| Ex. 17 | ◎ | ◎ | ◎ | ◎ | ◎ | ◎ | ◎ |
| Ex. 18 | ◎ | ◎ | ◎ | ◎ | ◎ | ◎ | ◎ |
| Ex. 19 | ◎ | ◎ | ◎ | ◎ | ◎ | ◎ | ◎ |
| Ex. 20 | ◎ | ◎ | ◎ | ◎ | ◎ | ◎ | ◎ |
| Comp. Ex. 9 | ◎ | Δ | Δ | ○ | ○ | ◎ | ◎ |
| Comp. Ex. 10 | ◎ | X | X | ○ | Δ | ◎ | ◎ |
| Comp. Ex. 11 | ◎ | ◎ | ◎ | ○ | Δ | X | X |
| Comp. Ex. 12 | ○ | X | X | ◎ | ◎ | ◎ | ◎ |
| Comp. Ex. 13 | ◎ | ◎ | ◎ | X | X | ◎ | ◎ |
| Comp. Ex. 14 | ○ | X | X | ◎ | ◎ | ◎ | ◎ |
| Comp. Ex. 15 | ◎ | ◎ | ◎ | X | X | Δ | X |
| Comp. Ex. 16 | ○ | X | X | ◎ | ◎ | ◎ | ◎ |

Each odor eliminating cloth manufactured as mentioned above was evaluated in odor elimination performance according of the following test method. The results are shown in Tables 2 and 4.

<Odor Elimination Performance Test>

(Ammonia Odor Elimination Performance)

After putting a test piece (10×10 cm square) cut out from each odor eliminating cloth into a bag having an interior content of 500 mL, an ammonia gas was injected therein so that the concentration became 200 ppm in the bag. After passing one hour since the injection, the ammonia remaining concentration was measured. From this measured value, the total amount that each test piece decomposed and removed the ammonia gas was calculated, and the ammonia elimination ratio (%) was calculated.

(Hydrogen Sulfide Odor Elimination Performance)

The hydrogen sulfide elimination ratio (%) was calculated in the same manner as in the aforementioned ammonia odor elimination measurement except that a hydrogen sulfide gas was injected in place of the ammonia gas so that the concentration become 20 ppm.

(Methyl Mercaptan Odor Elimination Performance)

The methyl mercaptan odor elimination ratio (%) was calculated in the same manner as in the aforementioned ammonia odor elimination measurement except that a methyl mercaptan gas was injected in place of the ammonia gas so that the concentration become 40 ppm in the bag and the gas remaining concentration was measured 4 hours later after the injection.

(Acetic Acid Odor Elimination Performance)

The acetic acid elimination ratio (%) was calculated in the same manner as in the aforementioned ammonia odor elimination measurement except that a acetic acid gas was injected in place of the ammonia gas so that the concentration become 100 ppm.

(Acetaldehyde Odor Elimination Performance)

The acetaldehyde odor elimination ratio (%) was calculated in the same manner as in the aforementioned ammonia odor elimination measurement except that a acetaldehyde gas was injected in place of the ammonia gas so that the concentration become 80 ppm in the bag and the gas remaining concentration was measured 4 hours later after the injection.

(Formaldehyde Odor Elimination Performance)

The formaldehyde odor elimination ratio (%) was calculated in the same manner as in the aforementioned ammonia odor elimination measurement except that a formaldehyde gas was injected in place of the ammonia gas so that the concentration become 80 ppm in the bag and the gas remaining concentration was measured 4 hours later after the injection.

(Trimethylamine Odor Elimination Performance)

The trimethylamine odor elimination ratio (%) was calculated in the same manner as in the aforementioned ammonia odor elimination measurement except that a trimethylamine gas was injected in place of the ammonia gas so that the concentration become 60 ppm in the bag.

The performance was evaluated as follows:
"⊚" denotes that the elimination ratio was 95% or more;
"○" denotes that the elimination ratio was 80% or more but less than 95%;
"Δ" denotes that the elimination ratio was 70% or more but less than 80%; and
"x" denotes that the elimination ratio was less than 70%.

As will be apparent from Tables 2 and 4, in the odor elimination cloths of Examples 1 to 20 according to this invention, excellent odor elimination effects were exerted to any types of odors of basic gases (e.g., ammonia gases, trimethylamine gases), acidic gases (e.g., acetic acid gases), neutral gases (e.g., acetaldehyde gases, formaldehyde gases), and sulphur series gases (e.g., hydrogen sulfide gases, mercaptan series gases).

Furthermore, from the comparison of the odor elimination performance of Example 1 and that of Example 5, in the odor eliminating cloth of Example 1 in which hydrazine derivative was fixed was further improved in natural gas elimination performance as compared with the odor eliminating cloth of Example 5 in which no hydrazine derivative was fixed.

Furthermore, from the comparison of the odor elimination performance of Example 10 and that of Example 16, in the odor eliminating cloth of Example 10 in which metal hydroxide was fixed was further improved in metal hydroxide gas elimination performance as compared with the odor eliminating cloth of Example 16 in which no metal hydroxide was fixed.

This application claims priority to Japanese Patent Application No. 2005-354249 filed on Dec. 8, 2005, the entire disclosure of which is incorporated herein by reference in its entirety.

It should be appreciated that the terms and descriptions herein are used only for explaining embodiments of the present invention, and the present invention is not limited to them. The present invention permits any design modifications within the scope of the present invention defined by the appended claims unless they deviate from its spirit of the present invention.

INDUSTRIAL APPLICABILITY

The odor eliminating cloth of this invention can be preferably used as, for example, a chair covering cloth, a curtain, a carpet, a wallpaper, or a vehicle interior material, but not limited thereto.

The invention claimed is:

1. A method of manufacturing an odor eliminating cloth, comprising:
   applying an aqueous solution of pH 6 to 8 containing: a binder resin; and an odor eliminating composition containing a zeolite, a zinc oxide, an inorganic silicon compound carrying a polyamine compound, and a dihydrazide sebacate to at least a part of a cloth; and thereafter drying the cloth, wherein the aqueous solution of pH 6 to 8 is applied to at least a part of the cloth having a surface of pH 6 to 8.

2. A method of manufacturing an odor eliminating cloth, comprising:
   applying an aqueous solution of pH 6 to 8 containing: a binder resin; and an odor eliminating composition containing a zeolite, a zinc oxide, an inorganic silicon compound carrying a polyamine compound, and a zirconium hydroxide to at least a part of a cloth; and thereafter drying the cloth, wherein the aqueous solution of pH 6 to 8 is applied to at least a part of the cloth having a surface of pH 6 to 8.

* * * * *